(12) United States Patent
Cao et al.

(10) Patent No.: US 9,302,971 B2
(45) Date of Patent: Apr. 5, 2016

(54) PROCESS TO PRODUCE TEREPHTHALIC ACID

(71) Applicant: ExxonMobil Chemical Patents Inc., Baytown, TX (US)

(72) Inventors: Guang Cao, Princeton, NJ (US); James R. Lattner, LaPorte, TX (US); Javier Guzman, Easton, PA (US); Shifang L. Luo, Kingwood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/515,823

(22) Filed: Oct. 16, 2014

(65) Prior Publication Data

US 2015/0126772 A1 May 7, 2015

Related U.S. Application Data

(60) Provisional application No. 61/898,521, filed on Nov. 1, 2013.

(51) Int. Cl.
| | |
|---|---|
| *C07C 51/265* | (2006.01) |
| *C07D 493/08* | (2006.01) |
| *C07C 45/66* | (2006.01) |
| *C07C 29/20* | (2006.01) |
| *C07C 29/19* | (2006.01) |
| *C07C 67/08* | (2006.01) |
| *C07D 307/46* | (2006.01) |
| *C07C 29/00* | (2006.01) |
| *C08K 5/00* | (2006.01) |
| *C07C 51/255* | (2006.01) |

(52) U.S. Cl.
CPC ............... *C07C 51/265* (2013.01); *C07C 29/00* (2013.01); *C07C 29/19* (2013.01); *C07C 29/20* (2013.01); *C07C 45/66* (2013.01); *C07C 51/255* (2013.01); *C07C 67/08* (2013.01); *C07D 307/46* (2013.01); *C07D 493/08* (2013.01); *C08K 5/0016* (2013.01); *C07C 2101/14* (2013.01)

(58) Field of Classification Search
None
See application file for complete search history.

(56) References Cited

U.S. PATENT DOCUMENTS

| 6,245,920 | B1 | 6/2001 | Morikawa et al. |
| 7,385,081 | B1 | 6/2008 | Gong |

(Continued)

FOREIGN PATENT DOCUMENTS

| WO | WO 2010/148081 | 12/2010 |
| WO | WO 2010/151346 | 12/2010 |

(Continued)

OTHER PUBLICATIONS

Leshkov, Y. R. et al. "*Production of Dimethylfuran for Liquid Fuels from Biomass-Derived Carbohydrates*", Nature Letters, Jun. 21, 2007, 447, pp. 982-985.

(Continued)

*Primary Examiner* — Sudhakar Katakam
*Assistant Examiner* — Jennifer C Sawyer

(57) ABSTRACT

This invention relates to the production of terephthalic acid by 1) cycloaddition of 2,5 substituted furan (such as 2,5-bis hydroxymethylfuran or 5-hydroxymethylfurfural) and ethylene, and 2) the subsequent oxidation of the dehydrated cycloaddition product to terephthalic acid. The invention relates more particularly to overall biobased pathways for making terephthalic acid from carbohydrates such as hexoses (e.g., glucose or fructose).

22 Claims, 7 Drawing Sheets

(56) References Cited

U.S. PATENT DOCUMENTS

| | | | |
|---|---|---|---|
| 2009/0124829 A1 | 5/2009 | Gong | |
| 2010/0331568 A1 | 12/2010 | Brandvold | |
| 2014/0350294 A1* | 11/2014 | Masuno | C07C 2/862 562/409 |

FOREIGN PATENT DOCUMENTS

| | | |
|---|---|---|
| WO | WO 2012/125218 | 9/2012 |
| WO | WO 2013/040514 | 3/2013 |
| WO | WO 2013/048248 | 4/2013 |

OTHER PUBLICATIONS

Williams, C. L. et al., "*Cycloaddition of Biomass-Derived Furans for Catalytic Production of Renewable p-Xylene*", ACS Catalysis, vol. 2 (6), pp. 935-939. 2012.

Zhao, H. et al., "*Metal Chlorides in Ionic Liquid Solvents Convert Sugars to 5-Hydroxymethylfurfural*", Science, Jun. 15, 2007, vol. 316, No. 5831, pp. 1597-1600.

* cited by examiner

PROCESS TO PRODUCE TEREPHTHALIC ACID

CROSS REFERENCE TO RELATED APPLICATIONS

This application claims the benefit of and priority to Ser. No. 61/898,521, filed Nov. 1, 2013, the disclosure of which is incorporated herein by reference in its entirety.

FIELD OF THE INVENTION

The present invention relates to the production of terephthalic acid from substituted furan and ethylene. The invention relates more particularly to overall biobased pathways for making terephthalic acid, from carbohydrates such as hexoses (e.g., glucose or fructose).

DESCRIPTION OF RELATED ART

Terephthalic acid is useful in the production of various polymers such as poly(ethylene terephthalate), poly(propylene terephthalate), and poly(butene terephthalate). Terephthalate polymers, such as poly(ethylene terephthalate) (PET), have many uses such as, for example, for making synthetic fibers and food-grade containers (e.g., beverage bottles). Major sources of terephthalic acid include oxidation of par-axylene streams that result from the refining of crude oil. Growing concerns related to the high costs of production of hydrocarbon fuel components and petrochemicals such as para-xylene have attracted attention to alternate sources such as renewable feedstocks. Renewable biomass resources are useful in the synthesis of substitutes for petroleum-derived product and there is an ongoing need for processes to synthesize, from bio-based feedstocks, additional compounds that are traditionally products of the petroleum and/or petrochemical industries. However, the difficulty in converting natural 6-carbon carbohydrate building blocks such as glucose or fructose to desirable end products has hindered progress in some important areas. Recent studies have shown the feasibility of converting hexose carbohydrates to 2,5-dimethylfuran (DMF). For example, Leshkov, Y. R. et al. report the production of 5-hydroxymethylfurfural (HMF) in high yields by the acid catalyzed dehydration of fructose, followed by the selective hydrogenation of HMF to DMF using a copper-based catalyst (NATURE, June 2007, (447): pp. 982-5). Also, Zhao, H. et al. describe the synthesis of HMF, starting with glucose, in the presence of a metal halide (e.g., chromium (II) chloride) in 1-alkyl-3-methylimidazolium chloride (SCIENCE, June 2007, (Vol. 316, No. 5831): pp. 1597-1600).

U.S. Pat. No. 7,385,081 describes the synthesis of terephthalic acid from carbohydrate derivatives. HMF is first oxidized to furan dicarboxylic acid (FDCA), which can then be esterified to 2,5-furan dicarboxylate. Ethylene is reacted with the FDCA or the dicarboxylate to form a bicyclic ether, which is then dehydrated to terephthalic acid or the terephthalic ester. This is referred to as Route I.

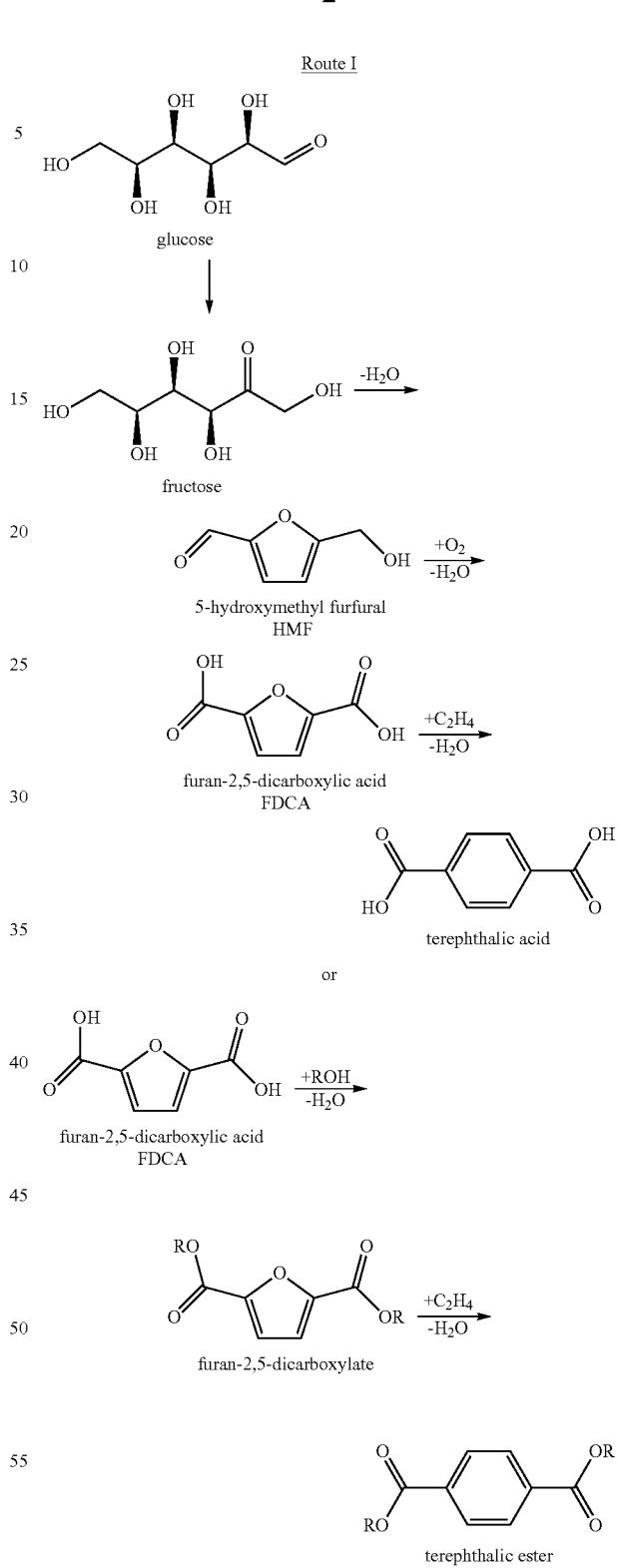

WO2010/151346 discloses the production of para-xylene by reacting DMF with ethylene under cycloaddition reaction conditions and in the presence of a catalyst. The p-xylene produced from this route can then be oxidized to terephthalic acid. This is referred to as Route II.

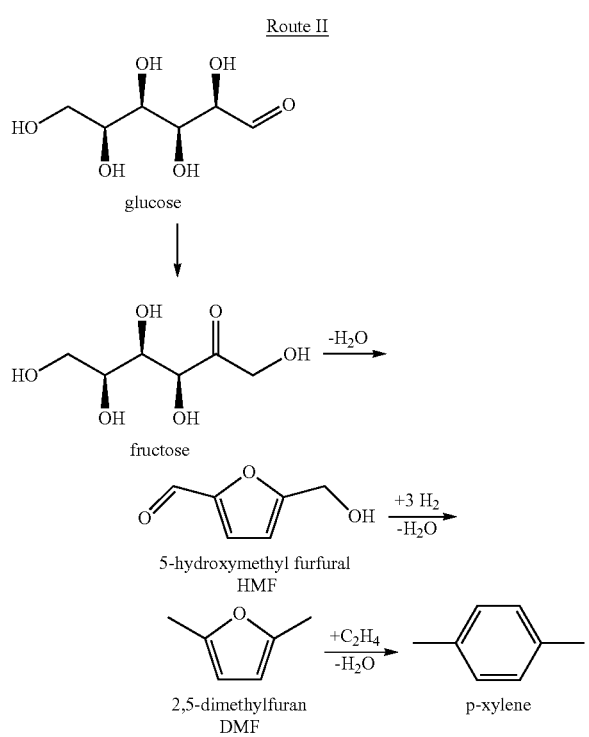

American Chemical Society Catalysis 2012, 2, pp. 935-939 discloses conversion of HMF to dimethylfuran which is then converted by cycloaddition to para-xylene.

Additional references of interest include: U.S. Pat. No. 6,245,920, WO2012/125218, WO2013/040514, and WO2013/048248. Methods for preparing terephthalic acid and terephthalic esters from certain biomass-derived starting materials are mentioned in WO 2010/148081 and WO 2010/151346.

The conversion of carbohydrates to terephthalic acid or ester via Route I suffers from low yields (less than 1% according to U.S. Pat. No. 7,385,081) in the ethylene cycloaddition step (to either the FDCA or the dimethyl ester of FDCA). The conversion of carbohydrates to p-xylene via Route II suffers from the need to add 3 molecules of hydrogen to each molecule of HMF to produce DMF. This added hydrogen is ultimately removed as water in the final oxidation step to terephthalic acid. What is needed is a route from carbohydrates to terephthalic acid that does not suffer from low yields (Route I) or the need to add multiple moles of hydrogen per carbohydrate molecule (Route II). What is also needed is an improvement to Route II, where the final oxidation step is facilitated by producing an intermediate molecule that is more active for oxidation to terephthalic acid than p-xylene.

SUMMARY OF THE INVENTION

This invention relates to the conversion of substituted furan (SF) compounds to terephthalic acid using a Diels Adler cycloaddition reaction with ethylene, particularly the conversion of 5-hydroxymethylfurfural (HMF) or 2,5-bis hydroxymethylfuran (BHMF) to a bicyclic ether which is then dehydrated to a 2,5 substituted phenyl which is then oxidized to terephthalic acid. Advantageously this pathway does not require the hydrogenation of the SF prior to the ethylene cycloaddition step.

In a first embodiment, this invention relates to the cycloaddition of ethylene to substituted furan represented by the formula:

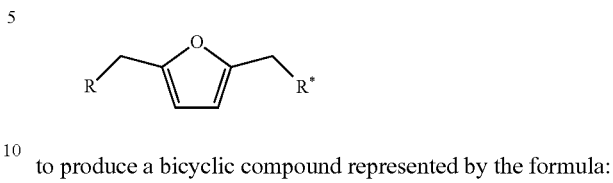

to produce a bicyclic compound represented by the formula:

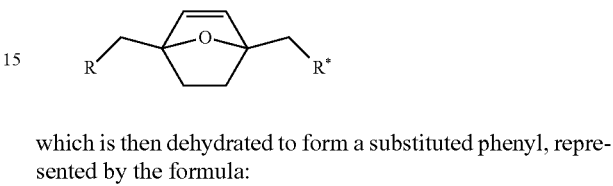

which is then dehydrated to form a substituted phenyl, represented by the formula:

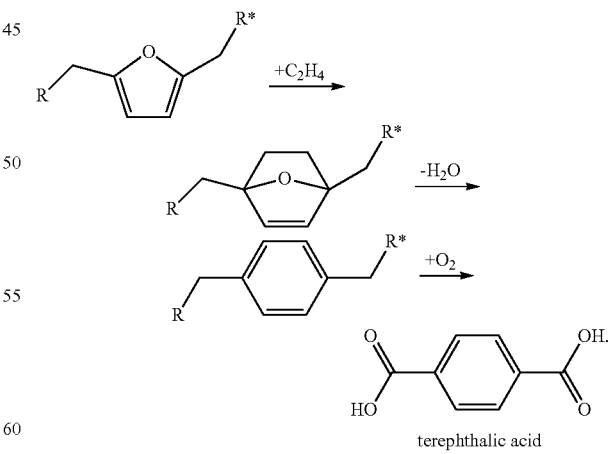

where R is =O, OH, OC(O)CH$_3$ and R* is =O, OH, OC(O)CH$_3$ or H, which can then be oxidized to terephthalic acid. In a preferred embodiment of the invention, the SF is not hydrogenated to the dialkyl (e.g., R and R* are not both alkyl groups) prior to the cycloaddition step. However, in some embodiments of the invention, the SF may be partially hydrogenated prior to the cycloaddition step. For example, HMF may be partially hydrogenated to BHMF prior to the cycloaddition step, but is not completely hydrogenated to 2,5-dimethylfuran. Alternately less than two molecules of hydrogen are added per SF molecule prior to the ethylene cycloaddition step.

As shown below, the cycloaddition of ethylene results in an intermediate bicyclic ether compound, which subsequently dehydrates to the 1,4-disubstituted phenyl ring. The 1,4-disubstituted phenyl can then be oxidized in to terephthalic acid:

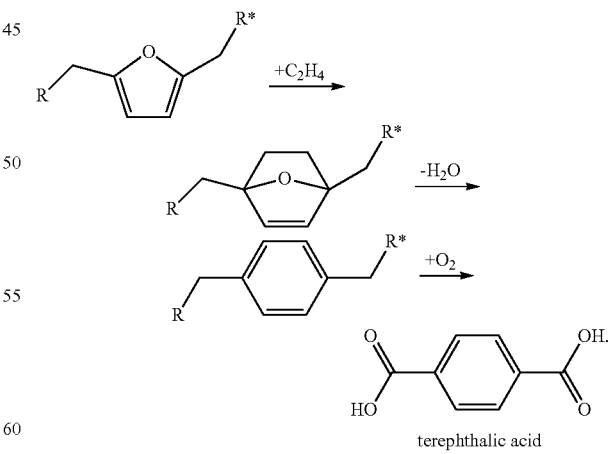

In one embodiment of the invention, ethylene is reacted with HMF without first adding hydrogen. The ethylene cycloaddition and subsequent dehydration of HMF gives 4-(hydroxymethyl)benzaldehyde (HMBA), as shown below, referred to as Route III:

Route III

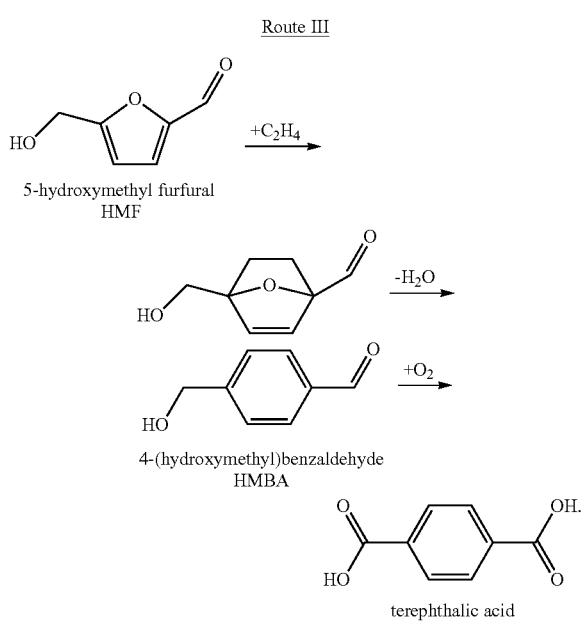

In another embodiment of the invention, the HMF molecule is first hydrogenated with one molecule of hydrogen to give BHMF. The ethylene cycloaddition and dehydration of BHMF gives 1,4-phenylenedimethanol (PDM), as shown below, referred to as Route IV:

Route IV

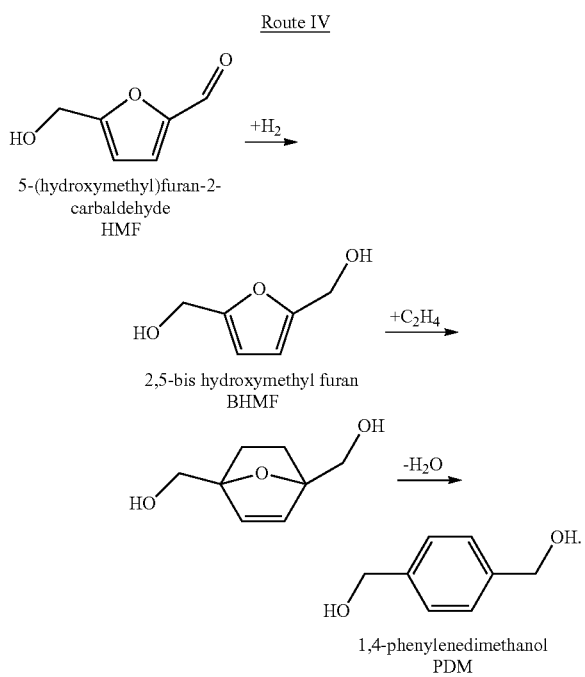

The 1,4-phenylenedimethanol (PDM) can be subsequently oxidized to terephthalic acid. Alternately, the PDM can be used in other applications, for example, by addition of organic acids to form diesters, or by polymerization with diacids to make polyesters.

In either of Routes III or IV, the product of the cycloaddition and dehydration reaction is more active for oxidation to terephthalic acid than the p-xylene intermediate produced by Route II. This is because the substituent groups (such as methyl) on the benzene ring in the HMBA or PDM intermediates are already partially oxidized, when produced from Routes III or IV respectively.

DETAILED DESCRIPTION

Figure 1:
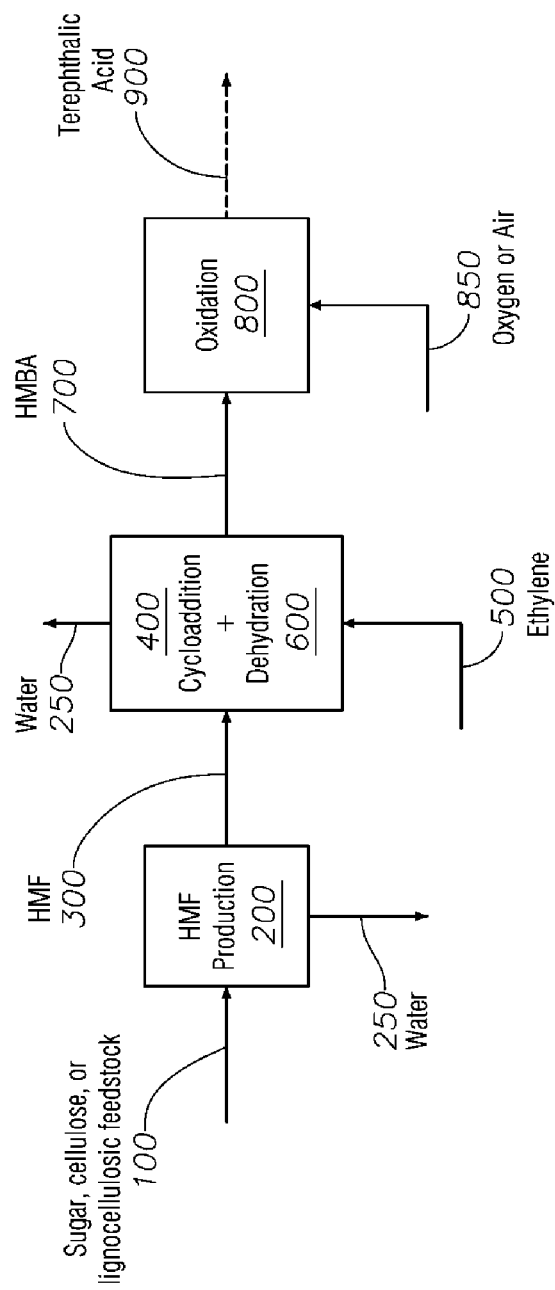
FIG. 1 shows a preferred embodiment of the invention according to Route III.

As used herein, the new notation for the Periodic Table Groups is used as described in *Chemical and Engineering News*, 63(5), p. 27 (1985).

The term "substituted" means that a hydrogen group has been replaced with a hydrocarbyl group, a heteroatom, or a heteroatom containing group. For example, 2,5 dimethyl furan is a furan group substituted with a methyl group at the 2 position and at the 5 position.

The terms "hydrocarbyl radical," "hydrocarbyl," and "hydrocarbyl group" are used interchangeably throughout this document. For purposes of this disclosure, "hydrocarbyl radical" is defined to be $C_1$ to $C_{20}$ radicals, that may be linear, branched, or cyclic (aromatic or non-aromatic), for example methyl, ethyl, ethenyl, and isomers of propyl, butyl, pentyl, hexyl, heptyl, octyl, nonyl, decyl, undecyl, and or dodecyl. An "alpha-olefin" is an olefin having a double bond at the alpha (or 1-) position and examples of α-olefins include ethylene, propylene, 1-butene, 1-pentene, 1-hexene, 1-heptene, 1-octene, 1-nonene, 1-decene, 1-undecene, and 1-dodecene. 5-hydroxymethylfurfural (HMF) is represented by the formula:

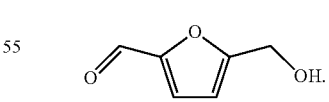

2,5-bis hydroxymethylfuran (BHMF) is represented by the formula:

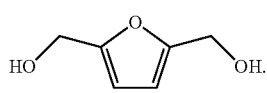

BHMF can be obtained by the hydrogenation of 5-hydroxymethylfurfural as disclosed in "Catalytic Hydrogenation over Platinum Metals," P. N. Rylander, Academic Press, New York, 1967, pp. 246-249.

The following abbreviations may be used through this specification: Me is methyl, Ph is phenyl, RT is room temperature which is defined as 25° C. unless otherwise specified, and tol is toluene.

The present invention is associated with processes for the conversion of substituted furan (SF) to bicyclic ether, which is then dehydrated to form a substituted phenyl which is then oxidized to terephthalic acid. Preferably, less than two molecules of hydrogen are added per SF molecule (preferably less than 1.5 molecules, preferably less than 1 molecule, preferably the SF is not hydrogenated) prior to conversion to the bicyclic ether. Alternately less than two moles of hydrogen are added per mole of SF, preferably less than 1.5 moles, preferably less than 1 mole, preferably the SF is not hydrogenated, prior to conversion to the bicyclic ether. More particularly, the cycloaddition of ethylene to an SF, such as BHMF or HMF, followed by dehydration of the bicyclic ether formed, then oxidation, can be used to produce terephthalic acid in good yields as well as save on production costs as costly hydrogenation step(s) are reduced or eliminated. In an alternate embodiment, the BHMF is combined with an acid, such as acetic acid, to produce a diester prior to the cycloaddition.

In a preferred embodiment, this invention relates to a terephthalic acid production process comprising reacting substituted furan with ethylene under cycloaddition reaction conditions and in the presence of a catalyst (such as activated carbon, acid washed activated carbon, silica, alumina, a zeolitic molecular sieve, or a non-zeolitic molecular sieve) to produce a bicyclic ether, which is then dehydrated to form a substituted phenyl and thereafter oxidizing the substituted phenyl to terephthalic acid, wherein the substituted furan is represented by the formula:

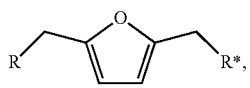

the bicyclic ether is represented by the formula:

and the substituted phenyl is represented by the formula:

where R is =O, OH, or OC(O)CH$_3$ and R* is =O, OH, OC(O)CH$_3$ or H, provided however that R and R* on the SF are not hydrogenated to the corresponding alkyl prior to the cycloaddition step. Thus, in a preferred embodiment of the invention, less than two moles of hydrogen are added per SF molecule prior to the ethylene cycloaddition step, preferably less that 1.5 moles, preferably less than 1 mole, preferably the SF is not hydrogenated prior to the cycloaddition step.

In a preferred embodiment of the invention, the substituted furan is represented by the formula:

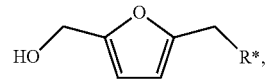

and/or the bicyclic ether is represented by the formula:

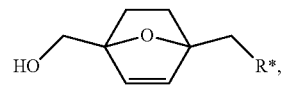

and/or the substituted phenyl is represented by the formula:

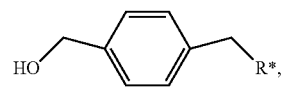

where R* is =O, H or OH, preferably =O or OH.

In a preferred embodiment of the invention, R and R* are the same. In another embodiment of the invention, R and R* are different. In a preferred embodiment of the invention, R is OH and R* is =O. In another embodiment of the invention, R and R* are OH or both R and R* are =O.

Advantageously, the SF (such as BHMF or HMF) starting material for the processes may be synthesized from carbohydrates, thereby providing a production route to terephthalic acid that relies at least partly on renewable feedstocks. For example, the use of glucose or fructose as a source of SF, such as BHMF or HMF, results in a process in which 6 of the 8 (75%) terephthalic acid carbon atoms originate from a carbohydrate. Moreover, if the ethylene used as a reactant in processes according to the invention is obtained from biomass ethanol, then the terephthalic acid produced is completely derived (i.e., all 8 of its 8 carbon atoms) from renewable feedstock.

The use of a solvent is useful for the formation of HMF from sugars, as well as for the ethylene cycloaddition reaction. For example, Leshkov, Y. R. et al. report the production of 5-hydroxymethylfurfural (HMF) in high yields by the acid catalyzed dehydration of fructose utilizing a biphasic reaction scheme with solvent extraction of the HMF product from the aqueous reaction media, for example with butanol as the solvent (NATURE, June 2007, (447): pp. 982-5). In the ethylene cycloaddition reaction, Chang et al. report the use of hexane solvent in the reaction of ethylene with DMF to produce p-xylene (GREEN CHEMISTRY (2013) DOI: 10.1039/c3gc40740c). In an additional embodiment, the same solvent is used in the HMF production step as in the ethylene cylcloaddition step. When the HMF is hydrogenated (with less than two moles of hydrogen per mole of HMF), the same solvent is used in all three steps. In a further embodiment, the solvent used is the same material produced in the ethylene cycloaddition and dehydration reaction, for example, HMBA in Route III and PDM in Route IV.

In the cycloaddition/dehydration step, the presence of water in the reaction mixture can be detrimental, as it can hydrolize the furan ring and/or slow or limit the dehydration reaction. In another embodiment, water is continuously removed from the reaction mixture by circulating excess ethylene through the reacting fluid, condensing and separating water from the gaseous ethylene effluent, and returning the unreacted ethylene vapor to the reaction mixture.

Embodiments of the invention are directed to terephthalic acid production processes comprising reacting substituted furan, such as BHMF or HMF, with ethylene under cycloaddition reaction conditions, preferably in the presence of a catalyst to produce a bicyclic ether, which is then dehydrated to produce a substituted phenyl which is then oxidized to terephthalic acid. Representative cycloaddition reaction conditions include a temperature from about 100° C. (212° F.) to about 300° C. (572° F.), an ethylene partial pressure from about 1000 kPa (145 psig) to about 10,000 kPa (14500 psig), and a reactor residence time from about 1 hour to about 48 hours. The processes may be performed batch-wise or in a continuous manner, for example by passing the SF, such as BHMF or HMF and ethylene reactants continuously over a fixed bed of catalyst. A representative catalyst is activated carbon (e.g., in a solid, powder form), and particularly carbon that has been activated by washing with an acid such as $H_3PO_4$. Other solid materials, and particularly those having a high surface area (e.g., zeolitic or non-zeolitic molecular sieves) and/or adsorptive capacity for the aromatic and olefinic feed components, may also be used as catalysts. Any of these catalysts may optionally be promoted with an alkali or alkaline earth metal promoter.

The cycloaddition reaction conditions and catalyst can provide at least about 50% conversion of the SF, such as BHMF or HMF, with terephthalic acid representing at least about 60%, on a molar basis, of the converted furan (i.e., at least about 60% selectivity to terephthalic acid, or at least about 0.6 moles of terephthalic acid produced for each mole of SF converted).

Therefore, according to embodiments of the invention, the conversion of a hexose such as glucose or fructose to SF, such as HMF or BHMF followed by cycloaddition, then oxidation to terephthalic acid provides a basis for terephthalic acid production using at least one renewable carbohydrate feedstock. Particularly useful embodiments of the invention are directed to carbohydrate based processes for producing terephalic acid comprising converting a hexose such as glucose or fructose to HMF or BHMF and then cycloaddition with ethylene to produce a substituted phenyl, which is then oxidized to terephthalic acid.

Without being bound by theory, the reaction is believed to proceed through the Diels-Alder cycloaddition of ethylene to the furan ring of HMF or BHMF, followed by ring opening with the elimination of water (dehydration) to generate a bisubstituted phenyl. Suitable catalysts and reaction conditions can improve productivity or yield, especially compared to thermal or non-catalytic reactions. The terms "catalyst" and "catalytic" are meant to encompass agents that reduce the activation energy needed for a desired reaction, as well as promoters that enhance the effectiveness of such agents.

Suitable catalysts include carbon and particularly activated carbon having a high surface area, for example of at least about 700 square meters per gram ($m^2$/gram), as measured according to the BET method (ASTM 6556-09). Generally, the surface area is in the range from about 700 to about 3000 $m^2$/gram and often from about 700 to about 1500 $m^2$/gram. Catalysts of particular interest include carbon that is activated by washing with an acid, for example, phosphoric acid, to provide the high surface area in these representative ranges and a possibly a number of other desirable properties. Such properties include a total oxygen content of at least about 1% by weight (e.g., in the range from about 1% to about 20%, and often from about 1% to about 10%, by weight).

Thermal processing or activation can also be used to obtain porous carbon particles having a large internal surface area. Regardless of whether the activation is performed chemically or thermally, the activated carbon particles may be granular, spherical, pelletized, or powdered, as supplied by a number of commercial manufacturers, including Norit Americas, Inc. (Marshall, Tex. USA), Japan EnviroChemicals (Tokyo, Japan), Jacobi Carbons AB (Kalmar, Sweden), and Calgon Carbon Corporation (Pittsburg, Pa.). A representative average particle size of a powdered activated carbon that is used in the methods described herein is less than about 300 microns (50 mesh) and often in the range from about 50 microns (300 mesh) to about 300 microns (50 mesh). Screening may be used in some cases to achieve a desired average particle size.

In general, the activated carbon is derived from an organic source, such as wood, ground coconut shells, etc. Various forms of activated carbon include a surface oxidized activated carbon, a graphite, a graphite oxide, or a carbon nanomaterial. Carbon nanomaterials include, but are not limited to, carbon nanotubes, carbon nanohorns, carbon nanofibers, buckyballs, etc. Activated carbon materials also include those having one or more surface modifications, for example, performed by covalently bonding of acidic or basic materials to control acidity and/or by the incorporation of one or more metals that is catalytically active for the conversion of adsorbed organic compounds. Such surface modifications can therefore supplement (promote) the catalytic activity of the activated carbon for the desired conversion.

In addition to activated carbon, a number of other materials having a relatively high BET surface area {e.g., at least about 200 $m^2$/gram, and often in the range from about 200 $m^2$/gram to about 500 $m^2$/gram), as well as having sufficient capacity for the adsorption of organic reactants, may be used as solid catalysts. These materials include inorganic oxides such as silica (e.g., in the form of a silica gel), alumina, zirconia, etc., as well as zeolitic molecular sieves and non-zeolitic molecular sieves. Zeolitic molecular sieves suitable for use as catalysts are crystalline aluminosilicates which in the calcined form may be represented by the general formula:

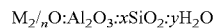

$$M_{2/n}O:Al_2O_3:xSiO_2:yH_2O$$

where M is a cation, such as H, alkaline metals (Na, K, etc.), alkaline earth metals (Mg, Ca, etc.) rare earth metals (La, Y, etc.), and transition metals, and $NH_4$, n is the valence of the cation, x has a value of from about 5 to 100, and y has a value of from about 2 to 10. Zeolites are described in detail by D. W. Breck, *Zeolite Molecular Sieves*, John Wiley and Sons, New York (1974), and elsewhere. In useful embodiments, the catalyst comprises a large pore zeolite, such as Y, zeolite β, mordenite, ZSM-12, ZSM-18, MCM-22, and/or MCM-49, and/or medium pore zeolites, such as ZSM-5, ZSM-11, ZSM-23, ZSM-48, and ZSM-57.

In useful embodiments, the catalyst comprises a zeolite, such as ZSM-5, zeolite beta, ITQ-13, MCM-22, MCM-49, ZSM-I 1, ZSM-12, ZSM-22, ZSM-23, ZSM-35, and ZSM-48, ZSM-57, preferably having been modified by steaming so as to have a Diffusion Parameter for 2,2 dimethylbutane of about 0.1-15 Sec-1 when measured at a temperature of 120° C. and a 2,2 dimethylbutane pressure of 60 torr (8 kPa). Alternately the catalyst may comprise ZSM-5, MCM-22, PSH-3, SSZ-25, ERB-I, ITQ-I, ITQ-2, ITQ-13, ITQ-39, MCM-36, MCM-49, MCM-56, Zeolite X, Zeolite Y, Zeolite Beta, and the like. Diffusion Parameter is defined at paragraph [0033] of WO 2013/009399.

Non-zeolitic molecular sieves include molecular sieves that are of the chemical composition, on an anhydrous basis, expressed by the empirical formula:

$$(EL_xAl_yP_z)q_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01, x+y+z=1, and q is oxygen. When EL is a mixture of metals, x represents the total amount of the element mixture present. Preferred elements (EL) are silicon, magnesium and cobalt, with silicon being especially preferred. These non-zeolitic molecular sieves are also referred to as "ELAPOs". The preparation of various ELAPOs are known in the art and described, for example, in U.S. Pat. No. 7,317,133, U.S. Pat. No. 5,191,141, U.S. Pat. No. 4,554,143, U.S. Pat. No. 4,440,871, U.S. Pat. No. 4,853,197, U.S. Pat. No. 4,793,984, U.S. Pat. No. 4,752,651, and U.S. Pat. No. 4,310,440.

As indicated above, any of the above solid catalysts may incorporate a metal promoter having catalytic activity for the desired conversion. Representative metals include alkali and alkaline earth metals, as well as rare earth and transition metals. Combinations of two or more metals may be used in conjunction with any of the solid catalysts described above (e.g., as support materials).

Alternately any catalyst disclosed in ACS Catalysis, 2012, 2, pp. 935-939 may be used herein.

The reaction of HMF and/or BHMF with ethylene proceeds in the presence of a catalyst as discussed above under suitable cycloaddition reaction conditions. Advantageously, the use of solvents (e.g., dimethylsulfoxide) that do not participate the desired reaction pathway can be minimized or even eliminated. According to some embodiments, therefore, the cycloaddition reaction conditions include a reaction mixture that is solvent-free or substantially solvent-free (i.e., contains less than about 10%, less than about 5%, or even less than about 1% of a solvent). Exemplary temperatures in the reactor or reaction zone in which the catalyst is disposed (e.g., in a batch reactor or as a fixed or moving bed in a continuous reaction system) are in the range from about 100° C. (212° F.) to about 300° C. (572° F.), and often from about 150° C. (302° F.) to about 225° C. (437° F.). Favorable cycloalkylation reaction conditions also include an ethylene partial pressure of at least about 1000 kPa (145 psig), generally in the range from about 1000 kPa (145 psig) to about 10,000 kPa (1450 psig), and often in the range from about 2000 kPa to about 5000 kPa. The total pressure is typically from about 2% to about 50% higher than the ethylene partial pressure, due to the contributions, to the overall pressure in the reactor or reaction zone, of (i) the vapor pressure of the SF (i.e. HMF and or BHMF) at the reaction temperature, and/or (ii) possible diluents and/or impurities (e.g., ethane).

Whether the reaction is carried out batchwise or continuously, the cycloaddition reaction conditions also generally include a reactor residence time in the range from about 1 hour to about 48 hours, and normally from about 3 hours to about 30 hours. The reactor residence time, however, may be significantly reduced in the case of a continuous process in which unconverted SF and/or ethylene are recycled to provide a relatively high overall conversion, even if the per-pass conversion is significantly less. Reactant SF may be continuously fed to a cycloaddition reaction zone, for example, at a liquid hourly space velocity (LHSV) from about 0.05 hr to about 5 hr. As is understood in the art, the Liquid Hourly Space Velocity (LHSV, expressed in units of hr) is the volumetric liquid flow rate over the catalyst bed divided by the bed volume and represents the equivalent number of catalyst bed volumes of liquid processed per hour. The LHSV is therefore closely related to the inverse of the reactor residence time.

The Diels-Alder cycloaddition of ethylene to the 2,5 disubstituted furan is facilitated if the substituents are both electron-donating groups. In 5-hydroxymethyl furfural, one of the substituents is a carbaldehyde, which is electron-withdrawing, while the other is an electron-donating hydroxymethyl group. Selective addition of one molecule of hydrogen to the carbaldehyde group on the HMF molecule will convert the electron-withdrawing carbonyl to an electron-donating hydroxymethyl group. The resulting 2,5-bis hydroxymethyl furan (BHMF) is more reactive than the 5-hydroxymethyl furfural (HMF) in the Diels-Alder cycloaddition reaction with ethylene as the dienophile, and the BHMF or HMF as the diene. The selective hydrogenation of furan-2-carbaldehyde (or furfural) to 2-furanmethanol (or furfuryl alcohol) is known to those in the art of the production of furfuryl alcohol. Early work by Kaufmann and Adams report high conversion and selectivity of furfural to furfuryl alcohol over reduced platinum catalysts (J. Am. Chem. Soc., December 1923, pp. 3029-3044). Conversion over nickel and palladium catalysts were also reported. In more recent work by Sharma et al, 100% conversion of furfural to furfuryl alcohol with 96% selectivity is reported over Cu:Zn:Cr:Zr catalyst (App. Cat A: Gen 454, pp. 127-136 (2013) DOI: 10.1016/j.apcata.2012.12.010). Similar catalysts and conditions may be used to convert 5-hydroxymethyl furfural to 2,5-bis hydroxymethyl furan.

In an exemplary continuous process, the reactants SF and ethylene are continuously fed to one or more reactors containing a fixed bed of the catalyst (e.g., in a swing-bed reactor system having multiple fixed bed reactors), and a product comprising the converted 1,4 disubstituted phenyl (such as HMBA or PDM) is continuously withdrawn together with unconverted reactants and reaction byproducts. The unconverted materials are preferably separated, for example, based on differences in their relative volatility using one or more separation operations (e.g., flash separation or distillation) employing a single stage or multiple stages of vapor-liquid equilibrium contacting.

According to a specific embodiment, unconverted ethylene, together with low boiling byproducts and impurities, is separated from the cycloaddition reaction zone effluent using a single-stage flash separation. The liquid bottoms product of this flash separation is then passed to at least one multi-stage distillation column to separately recover purified 1,4 disubstituted phenyl and unconverted SF. The unconverted SF and/or unconverted ethylene may be recycled to the cycloaddition reaction zone, optionally after purging a portion of either or both of these streams to limit the accumulation of byproducts having similar boiling points. In a particular embodiment, excess ethylene is added to the reactor to strip water from the reaction zone; this water is condensed and separated from the ethylene before being recycled to the reactor. According to a particular continuous operation, the flow rate of ethylene reactant to the cycloaddition reactor or reaction zone is controlled to maintain a desired total pressure. Such an operation based on pressure demand ensures that ethylene is fed at a rate that matches essentially its consumption plus losses due to dissolution and possibly a gas purge (vent).

Whether a batch or a continuous process is used for the catalytic conversion of SF to substituted phenyl, the cycloaddition reaction conditions generally provide a SF conversion (which may be a per-pass conversion in the cycloaddition reaction zone, in the case of operation with the recycle of unconverted SF) of at least about 50%, for example from about 50% to about 90% and often from about 50% to about 75%. The recycle of unconverted SF, for example to extinction or nearly extinction, can provide an overall conversion that is complete or nearly complete. Of the converted SF, the selectivity to substituted phenyl is generally at least about 60%, meaning that at least about 0.6 moles of substituted phenyl are produced for each mole of SF converted. Typical selectivities to substituted phenyl are from about 60% to about 95%. In view of these representative conversion and selectivity values, the overall yield of substituted phenyl is generally at least about 30%, typically from about 30% to about 90%, and often from about 90% to about 75%, of the theoretical yield based on complete conversion of SF with a stoichiometric amount (1:1 molar) of ethylene to substituted phenyl and no byproduct formation.

After the SF is combined with the ethylene and the addition catalyst a bicyclic ether is formed. That ether is then preferably dehydrated to form the substituted phenyl. The bicyclic compound can go through dehydration in the same reaction step and in the presence of the same catalyst, and at the same conditions as the ethylene cycloaddition reaction.

After the SF is combined with the ethylene and the addition catalyst a bicyclic ether is formed. That ether is then preferably dehydrated to form the substituted phenyl which is then oxidized to terephthalic acid. The substituted phenyl can be oxidized to terephthalic acid using the same process that is used to oxidize p-xylene to terephthalic acid. It is expected that the oxidation reaction will be more facile with carbonyl or hydroxymethyl substitutions on the phenyl ring, relative to the methyl substituents in p-xylene. It is expected that the more facile reactivity of carbonyl or hydroxymethyl substituents will be translated to higher selectivity to terephthalic acid.

Alternately, the oxidation of the substituted phenyl to terephthalic acid can use different catalysts and processes than are practiced commercially for the oxidation of p-xylene. Such processes would take advantage of the higher reactivity of hydroxymethyl and aldehyde groups towards oxidation than the methyl groups of p-xylene. Many catalyst systems are known to be highly active and selective for the conversion of primary alcohols to carboxylic acids. For example, Gorbanev et al. show quantitative conversion of ethanol to acetic acid over $Ru(OH)_x/CeO_2$ catalysts in aqueous media. Other effective catalysts include mixed oxides of Mo, V, NB, as well as Pd (ACS Catalysis (2012) 2, 604-612, DOI: 10.1021/cs200554h).

The terephthalic acid is useful for preparing polyesters such as polyethylene terephthalate polymer (PET) using processes well known in the art. Once manufactured, the PET can be processed so as to produce a thermoplastic PET resin used in synthetic fibers, beverage, food and other liquid containers; thermoforming applications; and engineering resins often in combination with glass fiber.

Turning now to the figures, FIG. 1 shows a preferred embodiment of the invention according to Route III. A feedstock (100), preferably a renewable feedstock, such as sugar, cellulose, or lignocellulose is first converted to a 2,5-disubstituted furan compound (200) such as 5-hydroxymethyl furfural (HMF) (300), giving off water (250). The HMF is then subjected to cycloaddition conditions (400) with ethylene (500) to form a bicyclic ether intermediate, which subsequently dehydrates (600), giving off water (250) to a 1,4-disubstituted phenyl such as 4-(hydroxymethyl) benzaldehyde (HMBA)(700). This product can optionally be oxidized (800) in the presence of oxygen (850) to terephthalic acid (900).

Figure 2:
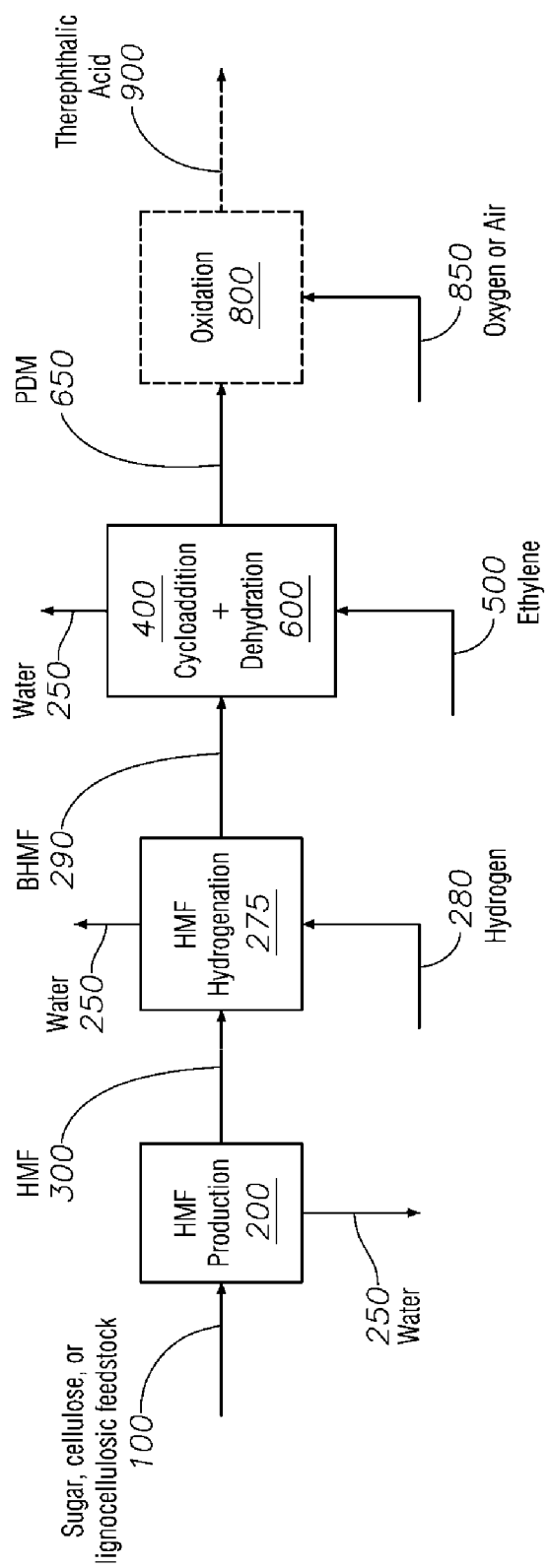
FIG. 2 shows a preferred embodiment of the invention according to Route IV.

FIG. 2 shows a preferred embodiment of the invention according to Route IV. A feedstock (100), preferably a renewable feedstock, such as sugar, cellulose, or lignocellulose is first converted to a 2,5-disubstituted furan compound (200) such as 5-hydroxymethyl furfural (HMF) (300). The HMF is then hydrogenated (275), in the presence of hydrogen (280), with less than two moles of hydrogen per mole of furan, to form a partially hydrogenated furan compound such as 2,5-bis hydroxymethyl furan (BHMF) (290). The partially hydrogenated furan is then subjected to cycloaddition 400 conditions with ethylene (500) to form a bicyclic ether intermediate, which subsequently dehydrates (600) to a 1,4-disubstituted phenyl such as 1,4-phenylene dimethanol (PDM) (650). This product can optionally be oxidized (800), in the presence of oxygen (850) to terephthalic acid (900).

Figure 3:
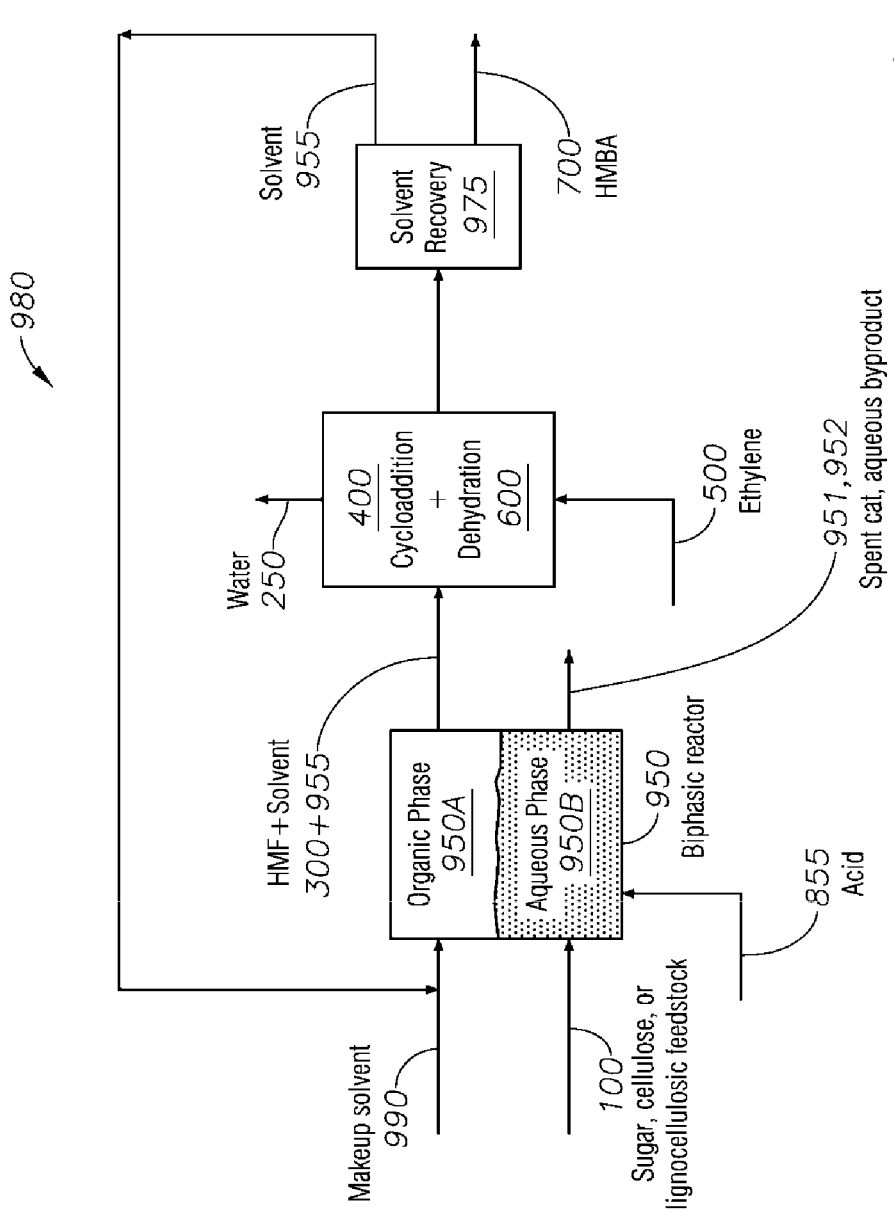
FIG. 3 shows a preferred embodiment of Route III where the same solvent is used for the HMF extraction as well as for the cycloaddition/dehydration reaction.

FIG. 3 shows a preferred embodiment of Route III where the same solvent is used for the HMF extraction as well as for the cycloaddition/dehydration reaction. In the first step, a biphasic reactor (950), having an organic phase (950A) and an aqueous phase (950B), is utilized as described by Leshkov, Y. R. et al. to convert the feedstock (100), preferably derived from biomass, typically using an acid catalyst (855), to HMF (300) and extract the HMF into an organic solvent (955) such as butanol, methyl isobutylketone, toluene, or mixtures thereof (NATURE, June 2007, (447) pp. 982-5). In the second step where the HMF (300) is reacted (400) with ethylene (500), the solvent is not separated and is utilized as the solvent in the ethylene cycloaddition step. Solvent is then separated from the product (975) and recycled to the first step (980). Additional solvent can be added as make-up solvent (990). Spent catalyst (951) and aqueous byproduct (952) can be removed intermittently or continuously from the biphasic reactor (950).

Figure 4:
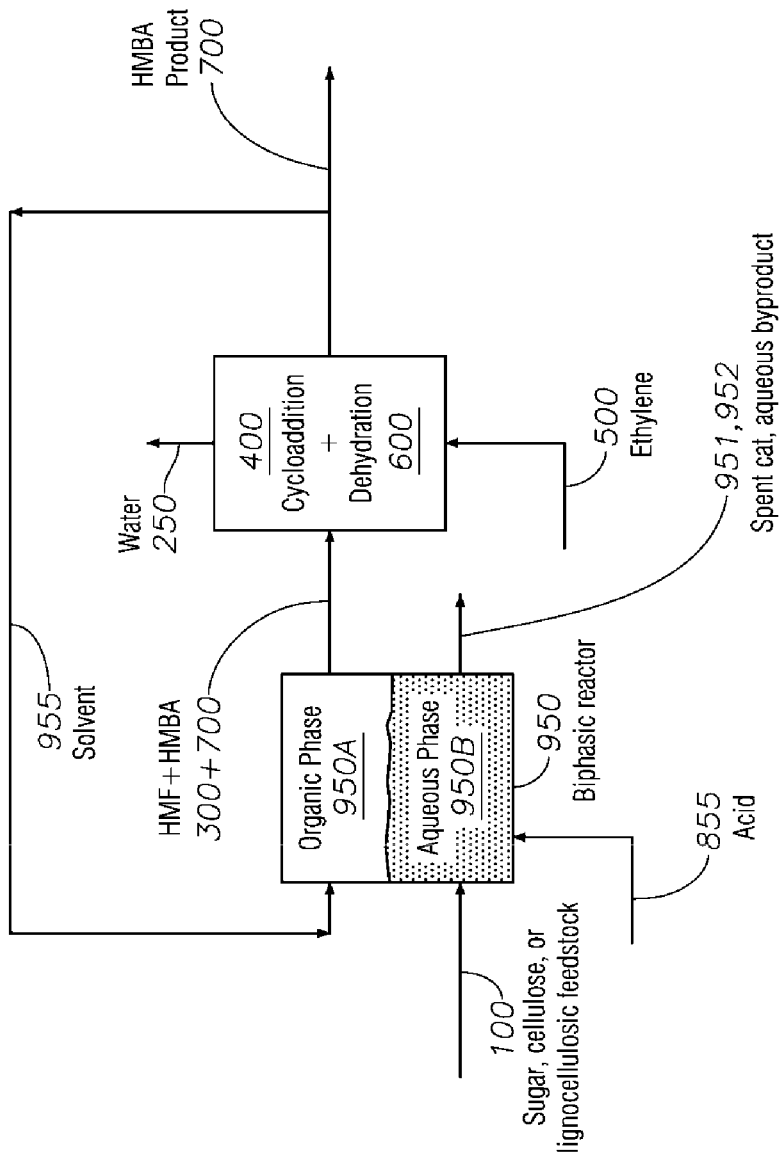
FIG. 4 shows a preferred embodiment of Route III where the HMBA is utilized as the solvent in both the HMF extraction and the ethylene cycloaddition/dehydration reactions.

FIG. 4 shows a preferred embodiment of Route III where the HMBA is utilized as the solvent in both the HMF extraction and the ethylene cycloaddition/dehydration reactions. The steps are the same as in FIG. 3, but where solvent separation from the HMBA product is avoided.

Figure 5:
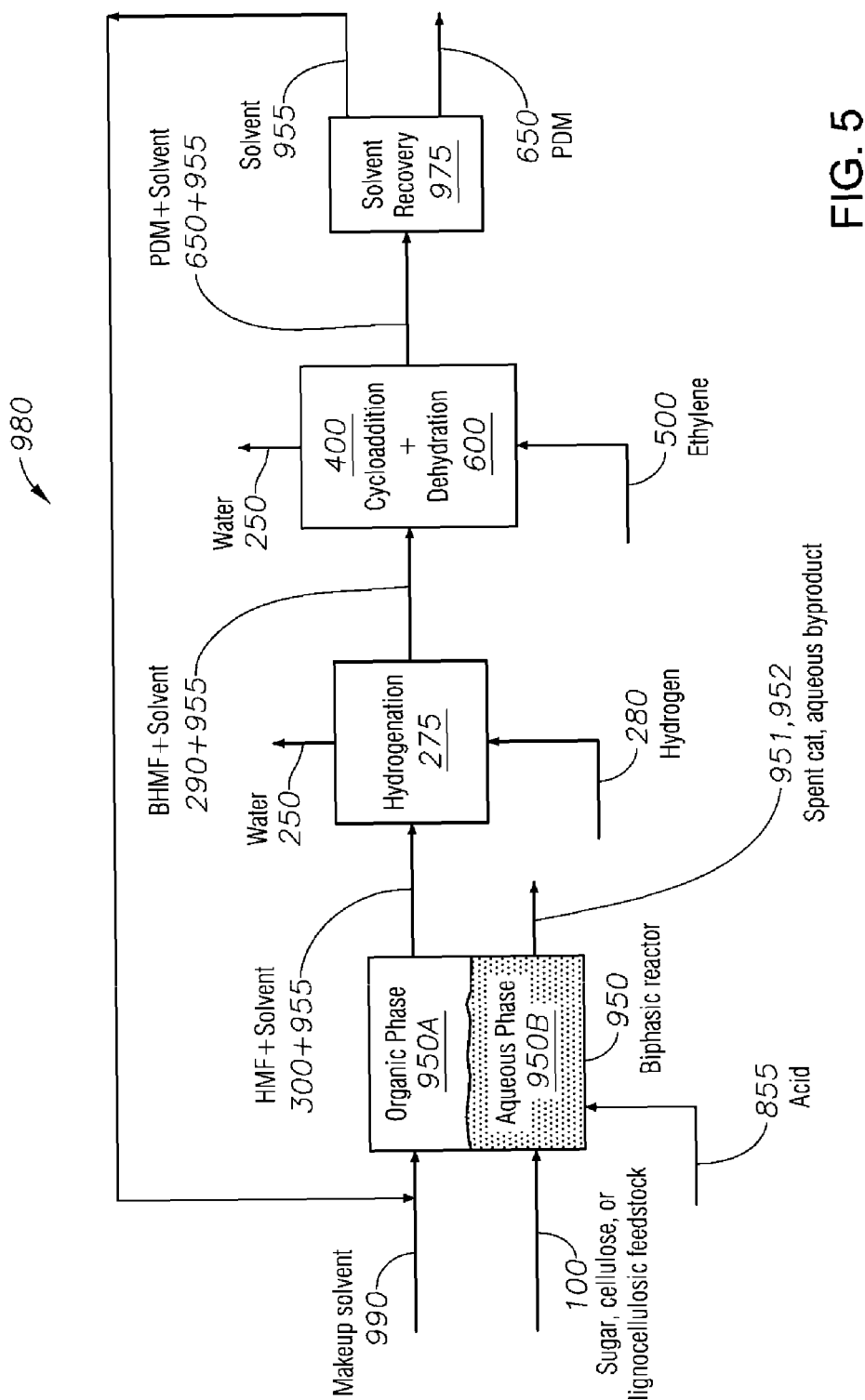
FIG. 5 shows a preferred embodiment of Route IV where the same solvent is used for the HMF extraction, the HMF hydrogenation, as well as for the cycloaddition/dehydration reaction.

FIG. 5 shows a preferred embodiment of Route IV where the same solvent is used for the HMF extraction, the HMF hydrogenation, as well as for the cycloaddition/dehydration reaction. In the first step, a biphasic reactor (950), having an organic phase (950A) and an aqueous phase (950B), is utilized as described by Leshkov, Y. R. et al. to convert the feedstock (100), preferably derived from biomass, typically using an acid catalyst (855), to HMF (300) and extract the HMF into an organic solvent (955) such as butanol, methyl isobutylketone, toluene, or mixtures thereof (NATURE, June 2007, (447) pp. 982-5). The solvent is not separated before the second step, where the HMF is hydrogenated (275) with less than two moles of hydrogen (280) per mole of HMF in the same solvent to form BHMF (290) and water (250). In the third step where the HMF is reacted (400) with ethylene (500) and dehydrated (600), the solvent is not separated and is utilized as the solvent in the ethylene cycloaddition step. Solvent (955) is then separated (975) from the product PDM (650) and recycled (980) to the first step. Additional solvent can be added as make-up solvent (990). Spent catalyst (951) and aqueous byproduct (952) can be removed intermittently or continuously from the biphasic reactor (950).

Figure 6:
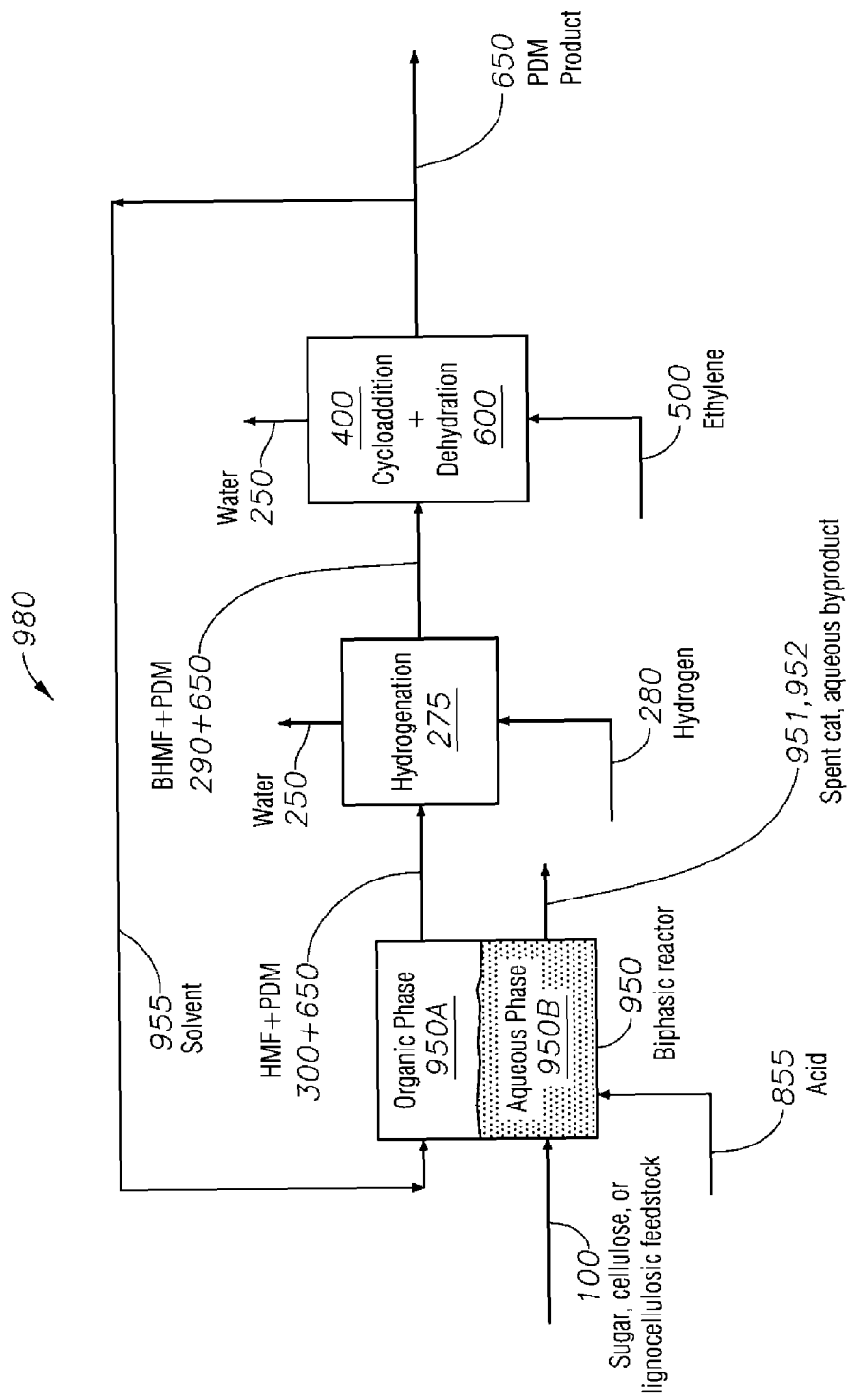
FIG. 6 shows a preferred embodiment of Route IV where the PDM is utilized as the solvent in the HMF extraction, the HMF hydrogenation, and the ethylene cycloaddition/dehydration reactions.

FIG. 6 shows a preferred embodiment of Route IV where the PDM is utilized as the solvent in the HMF extraction, the HMF hydrogenation, and the ethylene cycloaddition/dehydration reactions. The steps are the same as in FIG. 5, but where solvent separation from the PDM product is avoided.

Figure 7:
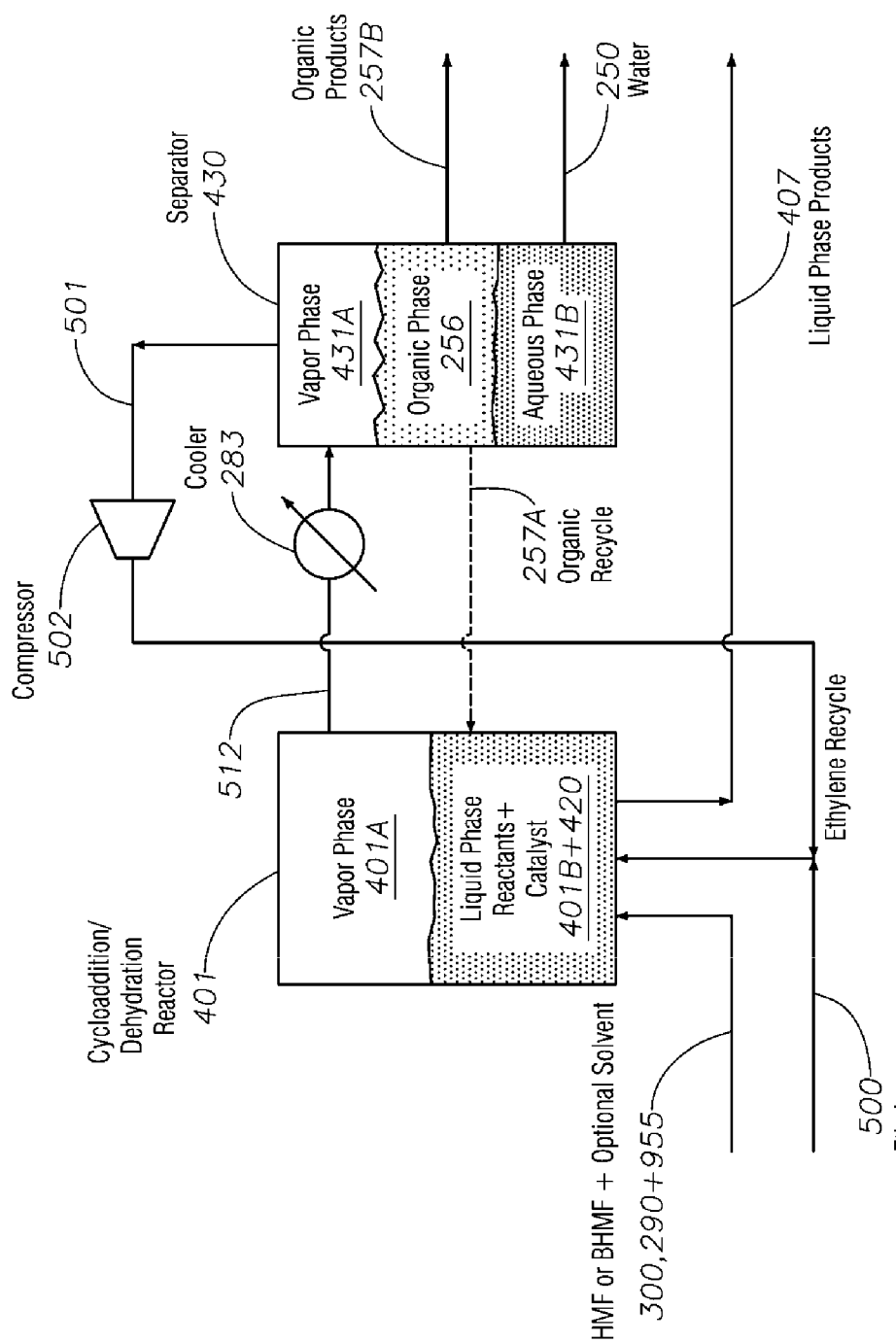
FIG. 7 shows a preferred embodiment for the cycloaddition/dehydration step for either Routes III or IV.

FIG. 7 shows a preferred embodiment for the cycloaddition/dehydration step for either Routes III or IV. The feed HMF (300) or BHMF (290) plus optional solvent (955) are fed to the Cycloaddition/Dehydration reactor (401), having a vapor phase (401A) and an aqueous phase (401B), and containing the catalyst (420). Ethylene (500) is added to the reaction step, where the excess ethylene is removed from the vapor phase of the reactor. The excess vapor acts to strip water from the liquid reaction mixture. The vapor effluent stream (512) is cooled (283), where water and some organic material are also stripped from the reactor condense. The water (250) is separated (430) from the unreacted ethylene vapor (431A) and any organic phase (256), and is withdrawn from the system. The ethylene vapor (501) is returned to the reactor via a compressor (502). Any condensed organic phase recovered in the separator may either be returned to the reactor (257A), or withdrawn as product (257B). Liquid phase products (407) are removed from the reactor (401).

In another embodiment of the invention, when R and R* on the substituted phenyl contain OH groups, the substituted phenyl can be hydrogenated to the cycloalkane and optionally used as a monomer in the production of polyester.

For example:

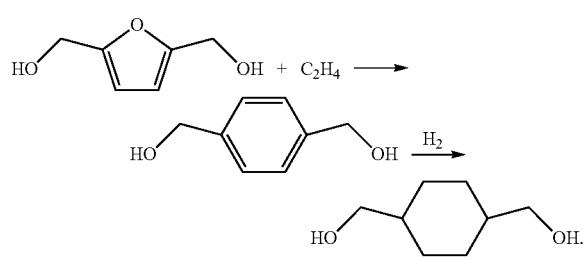

Ring saturation without hydrogenolysis of the hydroxymethyl group, such as the hydrogenation of 1,4-benzenedimethanol to 1,4-cyclohexanedimethanol, requires a selective catalyst (such as base metal catalysts Ni, Cu, or noble metal Rh, Pt, or multi-metallic metal catalysts). Typical conditions include hydrogen pressure of 100 to 5000 kPag and temperature of 0° C. to 200° C.

The two diol molecules above are useful as co-monomers, independently or together, for the production of polyesters. In particular, the 1,4-cyclohexanedimethanol is one of the most important co-monomers for production of polyethyleneterephthalate (PET). Currently, 1,4-cyclohexanedimethanol is produced via hydrogenation of terephthalic acid esters such as dimethylterephthalate at high temperature and high pressure.

In another embodiment, the diols produced here (aromatic or non-aromatic) can be esterified and used as plasticizers for polar polymers (such as polyvinylchloride and PET). For example 1,4-benzenedimethanol and or 1,4-cyclohexanedimethanol, can be combined with 2 moles of RCOOH (where R is $C_1$ to $C_{20}$ alkyl) and a catalyst (such as sulfuric acid) to obtain the diester (as shown below).

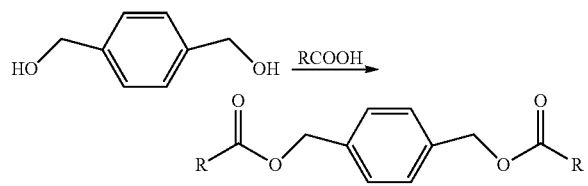

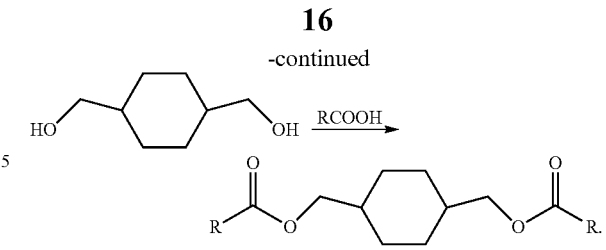

Such diesters are useful as plasticizers, particularly for polyvinylchloride and PET polymers.

A polar polymer is a polymer made from a monomer that contains a heteroatom.

In another embodiment this invention relates to:
1. A terephthalic acid production process comprising reacting substituted furan with ethylene under cycloaddition reaction conditions and in the presence of a catalyst to produce a bicyclic ether, dehydrating the bicyclic ether to produce a substituted phenyl and thereafter oxidizing the substituted phenyl to terephthalic acid, wherein the substituted furan is represented by the formula:

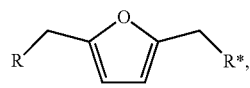

and the bicyclic ether is represented by the formula:

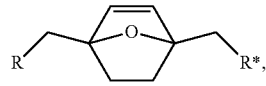

and the substituted phenyl is represented by the formula:

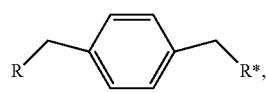

where R is =O, OH, OC(O)CH$_3$ and R* is =O, OH, OC(O)CH$_3$ or H, provided however that both substituents on the SF are not hydrogenated to the corresponding alkyl prior to the cycloaddition step.
2. The process of paragraph 1, wherein the cycloaddition reaction conditions include a temperature from about 100° C. to about 300° C.
3. The process of paragraphs 1 or 2, wherein the catalyst comprises activated carbon, silica, alumina, a zeolitic molecular sieve, or a non-zeolitic molecular sieve.
4. The process of paragraph 3, wherein the catalyst comprises activated carbon.
5. The process of paragraph 4, wherein the activated carbon is acid washed.
6. The process of any of paragraphs 1 to 5, wherein at least 6 of the carbon atoms of the terephthalic acid are derived from one or more annually renewable feedstocks.
7. The process of any of paragraphs 1 to 6, wherein the substituted furan is obtained from conversion of glucose or fructose.
8. The process of any of the above paragraphs 1 to 7, wherein the substituted furan comprises 5-hydroxymethylfurfural.
9. The process of any of the above paragraphs 1 to 8, wherein the substituted furan comprises 2,5-bis hydroxymethylfuran.

10. The process of paragraph 7, wherein the substituted furan is obtained from conversion of glucose or fructose to 5-hydroxymethylfurfural.

11. The process of paragraph 10, wherein the 5-hydroxymethylfurfural is not converted to 2,5-dimethylfuran prior to cycloaddition with ethylene.

12. A carbohydrate based process for producing terephthalic acid, comprising:
(a) converting a hexose to 5-hydroxymethylfurfural;
(b) reacting the 5-hydroxymethylfurfural with ethylene under cycloaddition reaction conditions and in the presence of a catalyst to produce a dicyclic ether, then dehydrating to produce a compound represented by the formula (I):

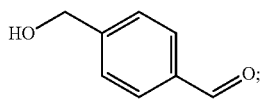

(I)

and
(c) oxidizing the compound represented by the formula (I) with oxygen to produce terephthalic acid; wherein the 5-hydroxymethylfurfural is not converted to 2,5-dimethylfuran prior to step (b).

13. A carbohydrate based process for producing terephthalic acid, comprising:
(a) converting a hexose to 2,5-bis hydroxymethylfuran;
(b) reacting the 2,5-bis hydroxymethylfuran with ethylene under cycloaddition reaction conditions and in the presence of a catalyst to produce a bicyclic ether, then dehydrating to produce a compound represented by the formula (II):

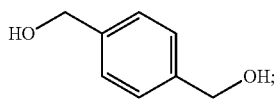

(II)

and
(c) oxidizing the compound represented by the formula (II) with oxygen to produce terephthalic acid; wherein the 2,5-bis hydroxymethylfuran is not converted to 2,5-dimethylfuran prior to step (b).

14. The process of paragraph 1, wherein the substituted furan is represented by the formula:

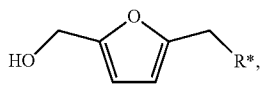

and and the bicyclic ether is represented by the formula:

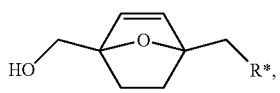

and the substituted phenyl is represented by the formula:

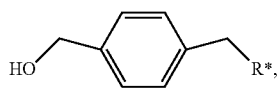

where R* is —C═O or —OH.

15. The process of any of the above paragraphs 1-14, wherein the substituted furan comprises 2,5-bis hydroxymethylfuran and the 2,5-bis hydroxymethylfuran is combined with an acid to produce a diester prior to the cycloaddition step.

16. The process of paragraph 14, wherein the acid is acetic acid.

17. The process of paragraph 1, wherein less than 1.5 moles of hydrogen are added per SF molecule prior to the cycloaddition step.

18. The process of paragraph 1, wherein less than 1 mole of hydrogen is added per SF molecule prior to the cycloaddition step.

19. A process to produce 1,4 cyclohexanedimethanol, comprising:
(a) converting a hexose to 2,5-bis hydroxymethylfuran;
(b) reacting the 2,5-bis hydroxymethylfuran with ethylene under cycloaddition reaction conditions and in the presence of a catalyst to produce a bicyclic ether, then dehydrating to produce a compound represented by the formula (II):

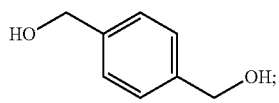

(II)

and
(c) hydrogenating the compound represented by the formula (II) with hydrogen in the presence of as base metal catalysts Ni, Cu, or noble metal Rh, Pt, or multi-metallic metal catalyst to produce 1,4 cyclohexanedimethanol; wherein the 2,5-bis hydroxymethylfuran is not converted to 2,5-dimethylfuran prior to step (b).

20. A process comprising:
(a) converting a hexose to 2,5-bis hydroxymethylfuran;
(b) reacting the 2,5-bis hydroxymethylfuran with ethylene under cycloaddition reaction conditions and in the presence of a catalyst to produce a bicyclic ether, then dehydrating to produce a compound represented by the formula (II):

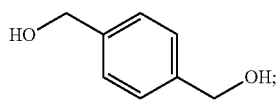

(II)

and
wherein the 2,5-bis hydroxymethylfuran is not converted to 2,5-dimethylfuran prior to step (b).

21. A method to produce a plasticized composition comprising combining a polar polymer with one or more diester compounds represented by the formula:

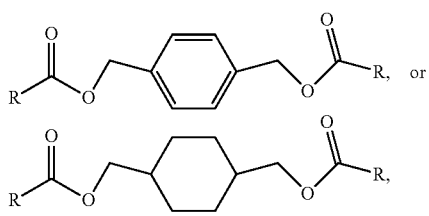

where R is a $C_1$ to $C_{20}$ alkyl group.

22. The method of paragraph 21, wherein the polymer is polyvinylchloride and PET polymers.
23. The method of paragraph 21, wherein the diester compound is derived from 1,4-benzenedimethanol and or 1,4-cyclohexanedimethanol, and the 1,4-benzenedimethanol is obtained by:
   (a) converting a hexose to 2,5-bis hydroxymethylfuran;
   (b) reacting the 2,5-bis hydroxymethylfuran with ethylene under cycloaddition reaction conditions and in the presence of a catalyst to produce a bicyclic ether, then dehydrating to produce a compound represented by the formula (II):

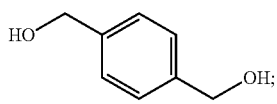 (II)

or 1,4-cyclohexanedimethanol is obtained by further hydrogenating the compound represented by the formula (II) with hydrogen in the presence of base metal or noble metal (mono- or multi-metallic) catalyst to produce 1,4 cyclohexanedimethanol; wherein the 2,5-bis hydroxymethylfuran is not converted to 2,5-dimethylfuran prior to step (b).

24. A process for production of terephthalic acid comprising:
   1) converting hexose to substituted furan in a biphasic reactor, said reactor having a having an organic phase and an aqueous phase;
   2) using an organic solvent to extract the substituted furan from the material produced by the biphasic reactor;
   3) transporting the combination of solvent and substituted furan to a cycloaddition reactor where, in the presence of the solvent, the substituted furan is reacted with ethylene under cycloaddition reaction conditions and in the presence of a catalyst to produce a bicyclic ether,
   4) thereafter, in the presence of the solvent, dehydrating the bicyclic ether to produce a substituted phenyl;
   5) recovering the solvent and recycling the solvent to step 2; and
   6) thereafter oxidizing the substituted phenyl to terephthalic acid, wherein the substituted furan is represented by the formula:

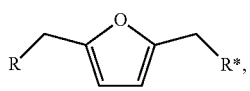

and the bicyclic ether is represented by the formula:

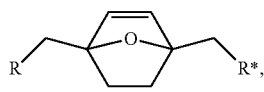

and the substituted phenyl is represented by the formula:

where R is =O, OH, or $OC(O)CH_3$ and R* is =O, OH, $OC(O)CH_3$ or H, provided however that the R and R* substituents on the substituted furan are not both hydrogenated to the corresponding alkyl prior to the cycloaddition step.

25. The process of paragraph 24 wherein (hydroxymethyl) benzaldehyde is utilized as the solvent in both the substituted furan extraction and the ethylene cycloaddition/dehydration reactions.

26. A process for production of terephthalic acid comprising:
   1) converting hexose to substituted furan in a biphasic reactor, said reactor having a having an organic phase and an aqueous phase;
   2) using an organic solvent to extract the substituted furan from the material produced by the biphasic reactor;
   3) combining, in the presence of the solvent, the substituted furan with less than 2 moles of hydrogen per mole of substituted furan to partially hydrogenate the substituted furan;
   4) transporting the combination of solvent and partially hydrogenated substituted furan to a cycloaddition reactor where, in the presence of the solvent, the substituted furan is reacted with ethylene under cycloaddition reaction conditions and in the presence of a catalyst to produce a bicyclic ether,
   5) thereafter, in the presence of the solvent, dehydrating the bicyclic ether to produce a substituted phenyl;
   6) recovering the solvent and recycling the solvent to step 2; and
   7) thereafter oxidizing the substituted phenyl to terephthalic acid, wherein the substituted furan is represented by the formula:

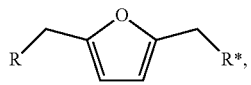

and the bicyclic ether is represented by the formula:

and the substituted phenyl is represented by the formula:

where R is =O, OH, or $OC(O)CH_3$ and R* is =O, OH, $OC(O)CH_3$ or H, provided however that the R and R* substituents on the substituted furan are not both hydrogenated to the corresponding alkyl prior to the cycloaddition step.

27. The process of paragraph 26 wherein 1,4-phenylenedimethanol is utilized as the solvent in both the substituted furan extraction and the ethylene cycloaddition/dehydration reactions.

28. The process of paragraph 1 wherein:
  1) the substituted furan plus optional solvent are fed to a Cycloaddition/Dehydration reactor, having a vapor phase and an aqueous phase, said reactor containing catalyst;
  2) ethylene is added to the reaction step, and the excess ethylene is removed from the vapor phase of the reactor;
  3) the vapor effluent stream is cooled and water is separated from unreacted ethylene vapor and any organic phase;
  4) the water is withdrawn from the system and the ethylene vapor is returned to the Cycloaddition/Dehydration reactor.

PROPHETIC EXAMPLES

Prophetic Example 1

Non-Catalytic Conversion of HMF to HMBA 100 mL of 1.0M HMF in 2-butanol is charged to an autoclave having a volume of 160 mL fitted with a gas inlet, thermocouple, pressure transducer, and magnetic stir bar. The autoclave is sealed, pressurized at room temperature with ethylene, and heated to a reaction temperature of 250° C. The reaction is allowed to run for a 24-hour reaction period while maintaining ethylene pressure in the autoclave of 6200 kPa. The reactor is then cooled and an analysis of the products is obtained.

Prophetic Example 2

Non-Catalytic Conversion of BHMF to PMB 100 mL of 1.0M BHMF in 2-butanol is charged to an autoclave having a volume of 160 mL fitted with a gas inlet, thermocouple, pressure transducer, and magnetic stir bar. The autoclave is sealed, pressurized at room temperature with ethylene, and heated to a reaction temperature of 250° C. The reaction is allowed to run for a 24-hour reaction period while maintaining ethylene pressure in the autoclave of 6200 kPa. The reactor is then cooled and an analysis of the products is obtained.

Prophetic Example 3

Catalytic Conversion of HMF to HMBA

The experimental procedure described in Prophetic Example 1 is followed, except that 0.5 g of solid catalyst in a particle form (granular or powdered) is added to the reactor prior to pressurization with ethylene. The experiments are described in Table 1.

TABLE 1

| Example | Catalyst | Si/Al ratio | Reaction temp (° C.) | Reactant |
|---|---|---|---|---|
| A | H-BEA | 12.5 | 250 | HMF |
| B | H-BEA | 19 | 250 | HMF |
| C | H-FAU | 2.6 | 250 | HMF |
| D | H-ZSM-5 | 15 | 250 | HMF |
| E | Niobic acid | | 250 | HMF |
| F | γ-$Al_2O_3$ | | 250 | HMF |

Prophetic Example 4

Catalytic Conversion of BHMF to PDM

The experimental procedure described in Prophetic Example 2 is followed, except that 0.5 g of solid catalyst in a particle form (granular or powdered) is added to the reactor prior to pressurization with ethylene. The experiments are described in Table 2.

TABLE 2

| Example | Catalyst | Si/Al ratio | Reaction temp (° C.) | Reactant |
|---|---|---|---|---|
| A | H-BEA | 12.5 | 250 | BHMF |
| B | H-BEA | 19 | 250 | BHMF |
| C | H-FAU | 2.6 | 250 | BHMF |
| D | H-ZSM-5 | 15 | 250 | BHMF |
| E | Niobic acid | | 250 | BHMF |
| F | γ-$Al_2O_3$ | | 250 | BHMF |

Prophetic Example 5

Catalytic Hydrogenation of HMF to BHMF 100 mL of 1.0M BHMF in 2-butanol is charged to an autoclave having a volume of 160 mL fitted with a gas inlet, thermocouple, pressure transducer, and magnetic stir bar. 0.5 g of 1% Pt on γ-$Al_2O_3$ catalyst is added to the autoclave. The autoclave is sealed, pressurized at room temperature with hydrogen, and heated to a reaction temperature of 150° C. The reaction is allowed to run for a while maintaining hydrogen pressure in the autoclave of 2000 kPa. The reactor is stopped by cooling and depressuring when one equivalent of hydrogen is consumed. An analysis of the products is then obtained.

Prophetic Example 6

Catalytic Conversion of BHMF to PDM in Various Solvents 100 mL of 1.0M BHMF in solvent (see Table 3) is charged to an autoclave having a volume of 160 mL fitted with a gas inlet, thermocouple, pressure transducer, and magnetic stir bar. 0.5 g of H-BEA catalyst having a Si/Al ratio of 12.5 is charged to the reactor. The autoclave is sealed, pressurized at room temperature with ethylene, and heated to a reaction temperature of 250° C. The reaction is allowed to run for a 24-hour reaction period while maintaining ethylene pressure in the autoclave of 6200 kPa. The reactor is then cooled and an analysis of the products is obtained.

TABLE 3

| Example | Solvent | Catalyst | Reaction temp (° C.) | Reactant |
|---|---|---|---|---|
| A | 2-butanol | H-BEA (12.5) | 250 | BHMF |
| B | toluene | H-BEA (12.5) | 250 | BHMF |
| C | 1:1 toluene:2-butanol | H-BEA (12.5) | 250 | BHMF |
| D | Methyl isobutyl ketone | H-BEA (12.5) | 250 | BHMF |
| E | HMBA | H-BEA (12.5) | 250 | BHMF |
| F | PDM | H-BEA (12.5) | 250 | BHMF |

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa. Thus, the term "comprising" encompasses the terms "consisting essentially of," "is," and "consisting of" and anyplace "comprising" is used "consisting essentially of," "is," or consisting of may be substituted therefor.

We claim:

1. A terephthalic acid production process comprising reacting substituted furan with ethylene under cycloaddition reaction conditions and in the presence of a catalyst to produce a bicyclic ether, dehydrating the bicyclic ether to produce a substituted phenyl and thereafter oxidizing the substituted phenyl to terephthalic acid, wherein the substituted furan is represented by the formula:

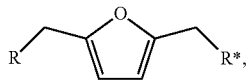

and the bicyclic ether is represented by the formula:

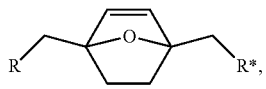

and the substituted phenyl is represented by the formula:

where R is =O, OH, or OC(O)CH$_3$ and R* is =O, OH, OC(O)CH$_3$ or H,
provided however that the R and R* substituents on the substituted furan are not both hydrogenated to the corresponding alkyl prior to the cycloaddition step, wherein less than 1.5 moles of hydrogen are added per substituted furan molecule prior to the cycloaddition step.

2. The process of claim 1, wherein the cycloaddition reaction conditions include a temperature from about 100° C. to about 300° C.

3. The process of claim 1, wherein the catalyst comprises activated carbon, silica, alumina, a zeolitic molecular sieve, or a non-zeolitic molecular sieve.

4. The process of claim 3, wherein the catalyst comprises activated carbon.

5. The process of claim 4, wherein the activated carbon is acid washed.

6. The process of claim 1, wherein at least 6 of the carbon atoms of the terephthalic acid are derived from one or more renewable feedstocks.

7. The process of claim 1, wherein the substituted furan is obtained from conversion of glucose or fructose.

8. The process of claim 1, wherein the substituted furan comprises 5-hydroxymethylfurfural.

9. The process of claim 1, wherein the substituted furan comprises 2,5-bis hydroxymethylfuran.

10. The process of claim 7, wherein the substituted furan is obtained from conversion of glucose or fructose to 5-hydroxymethylfurfural.

11. The process of claim 10, wherein the 5-hydroxymethylfurfural is not converted to 2,5-dimethylfuran prior to cycloaddition with ethylene.

12. A carbohydrate based process for producing terephthalic acid, comprising:
(a) converting a hexose to 5-hydroxymethylfurfural;
(b) reacting the 5-hydroxymethylfurfural with ethylene under cycloaddition reaction conditions and in the presence of a catalyst to produce a bicyclic ether, then dehydrating the bicyclic ether to produce a compound represented by the formula (I):

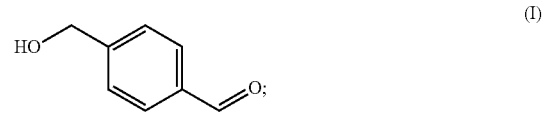

and
(c) oxidizing the compound represented by the formula (I) with oxygen to produce terephthalic acid; wherein the 5-hydroxymethylfurfural is not converted to 2,5-dimethylfuran prior to step (b), wherein less than 1.5 moles of hydrogen are added per 5-hydroxymethylfurfural prior to the cycloaddition step.

13. A carbohydrate based process for producing terephthalic acid, comprising:
(a) converting a hexose to 2,5-bis hydroxymethylfuran;
(b) reacting the 2,5-bis hydroxymethylfuran with ethylene under cycloaddition reaction conditions and in the presence of a catalyst to produce a bicyclic ether, then dehydrating the bicyclic ether to produce a compound represented by the formula (II):

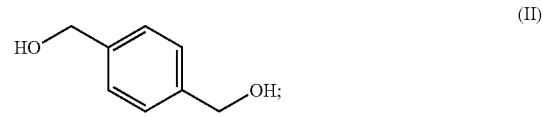

and
(c) oxidizing the compound represented by the formula (II) with oxygen to produce terephthalic acid; wherein the 2,5-bis hydroxymethylfuran is not converted to 2,5-dimethylfuran prior to step (b), wherein less than 1.5 moles of hydrogen are added per 2,5-bis hydroxymethylfuran prior to the cycloaddition step.

14. The process of claim 1, wherein the substituted furan is represented by the formula:

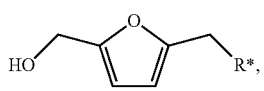

and
the bicyclic ether is represented by the formula:

and
the substituted phenyl is represented by the formula:

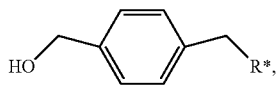

where R* is =O or —OH.

15. The process of claim 1, wherein the substituted furan comprises 2,5-bis hydroxymethylfuran and the 2,5-bis hydroxymethylfuran is combined with an acid to produce a diester prior to the cycloaddition step.

16. The process of claim 15, wherein the acid is acetic acid.

17. The process of claim 1, wherein less than 1 mole of hydrogen is added per substituted furan molecule prior to the cycloaddition step.

18. A process for production of terephthalic acid comprising:
 1) converting hexose to substituted furan in a biphasic reactor, said reactor having a having an organic phase and an aqueous phase;
 2) using an organic solvent to extract the substituted furan from the material produced by the biphasic reactor;
 3) transporting the combination of solvent and substituted furan to a cycloaddition reactor where, in the presence of the solvent, the substituted furan is reacted with ethylene under cycloaddition reaction conditions and in the presence of a catalyst to produce a bicyclic ether,
 4) thereafter, in the presence of the solvent, dehydrating the bicyclic ether to produce a substituted phenyl;
 5) recovering the solvent and recycling the solvent to step 2; and
 6) thereafter oxidizing the substituted phenyl to terephthalic acid, wherein the substituted furan is represented by the formula:

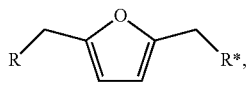

and the bicyclic ether is represented by the formula:

and the substituted phenyl is represented by the formula:

where R is =O, OH, or OC(O)CH$_3$ and R* is =O, OH, OC(O)CH$_3$ or H,
provided however that the R and R* substituents on the substituted furan are not both hydrogenated to the corresponding alkyl prior to the cycloaddition step, wherein less than 1.5 moles of hydrogen are added per substituted furan molecule prior to the cycloaddition step.

19. The process of claim 18, wherein (hydroxymethyl)benzaldehyde is utilized as the solvent in both the substituted furan extraction and the ethylene cycloaddition/dehydration reactions.

20. A process for production of terephthalic acid comprising:
 1) converting hexose to substituted furan in a biphasic reactor, said reactor having a having an organic phase and an aqueous phase;
 2) using an organic solvent to extract the substituted furan from the material produced by the biphasic reactor;
 3) combining, in the presence of the solvent, the substituted furan with less than 2 moles of hydrogen per mole of substituted furan to partially hydrogenate the substituted furan;
 4) transporting the combination of solvent and partially hydrogenated substituted furan to a cycloaddition reactor where, in the presence of the solvent, the substituted furan is reacted with ethylene under cycloaddition reaction conditions and in the presence of a catalyst to produce a bicyclic ether,
 5) thereafter, in the presence of the solvent, dehydrating the bicyclic ether to produce a substituted phenyl;
 6) recovering the solvent and recycling the solvent to step 2; and
 7) thereafter oxidizing the substituted phenyl to terephthalic acid, wherein the substituted furan is represented by the formula:

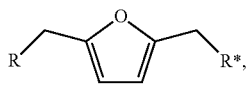

and the bicyclic ether is represented by the formula:

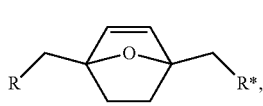

and the substituted phenyl is represented by the formula:

where R is =O, OH, or OC(O)CH$_3$ and R* is =O, OH, OC(O)CH$_3$ or H,
provided however that the R and R* substituents on the substituted furan are not both hydrogenated to the corresponding alkyl prior to the cycloaddition step.

21. The process of claim 20, wherein 1,4-phenylene-dimethanol is utilized as the solvent in both the substituted furan extraction and the ethylene cycloaddition/dehydration reactions.

22. The process of claim 1, wherein:
1) the substituted furan plus optional solvent are fed to a Cycloaddition/Dehydration reactor, having a vapor phase and an aqueous phase, said reactor containing catalyst;
2) ethylene is added to the reaction step, and the excess ethylene is removed from the vapor phase of the reactor;
3) the vapor effluent stream is cooled and water is separated from unreacted ethylene vapor and any organic phase;
4) the water is withdrawn from the system and the ethylene vapor is returned to the Cycloaddition/Dehydration reactor.

* * * * *